Figure 1:
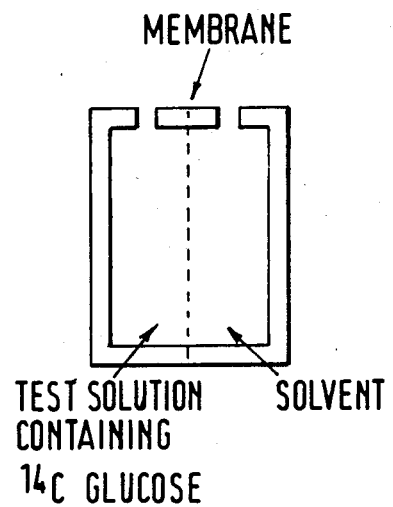

United States Patent [19]

Sugden

[11] Patent Number: 4,689,219

[45] Date of Patent: Aug. 25, 1987

[54] PHARMACEUTICAL COMPOSITIONS

[75] Inventor: Keith Sugden, Beverley, England

[73] Assignee: Reckitt & Colman Products Limited, England

[21] Appl. No.: 618,239

[22] Filed: Jun. 7, 1984

[30] Foreign Application Priority Data

Jun. 29, 1983 [GB] United Kingdom ............... 8317595

[51] Int. Cl.$^4$ .................. A61K 37/00; A61K 31/715
[52] U.S. Cl. ....................................... 424/80; 514/2; 514/54; 514/886
[58] Field of Search ............... 514/54, 2, 886; 424/80

[56] References Cited

U.S. PATENT DOCUMENTS 4,136,173  1/1979  Pramoda et al. .................. 424/177

FOREIGN PATENT DOCUMENTS 1108376   4/1968  United Kingdom .
1531987  11/1978  United Kingdom .

OTHER PUBLICATIONS

*Chemical Abstracts,* vol. 93 (1980) 44637n, vol. 96 (1982) 33848t.

*Primary Examiner*—Frederick E. Waddell
*Attorney, Agent, or Firm*—Bacon & Thomas

[57] ABSTRACT

Pharmaceutical compositions comprising mixtures of xanthan gum and locust bean gum in a specified range of ratios have been found to exhibit synergistic effects in an in vitro test model. Pharmaceutical compositions adapted for oral administration comprising mixtures of xanthan gum and locust bean gum in the range of ratios are described for use in the treatment of diabetes or of satiety.

9 Claims, 11 Drawing Figures

PHARMACEUTICAL COMPOSITIONS

This invention relates to pharmaceutical compositions and in particular to compositions for use in the treatment of diabetes or of satiety.

It is well known that certain unabsorbable plant polysaccharides such as guar gum and pectin, when administered in substantial quantities, can cause a reduction in the levels of glucose and cholesterol in healthy volunteers and in diabetic patients. Unfortunately in order to obtain the desired effects patients have to take large quantities of unpalatable gum. Thus in a study reported by Jenkins D. J. A. et al (Lancet 1976, 9774, 1086) patients received daily doses of 16.5 or 25.0 g guar gum.

During an investigation with other polysaccharides to evaluate their inhibitory effects on the diffusion of glucose across a membrane we found a synergistic effect when xanthan gum and locust bean gum were mixed in certain proportions. Our investigations of the mixtures were extended to include in vivo studies in the rat and in human volunteers which confirmed the blood glucose lowering properties.

According to this invention there is provided a pharmaceutical composition adapted for oral administration which comprises xanthan gum and locust bean gum in a weight:weight ratio of between 1:9 and 9:1.

In a preferred composition the ratio of xanthan gum to locust bean gum is between 1:3 and 3:1 and conveniently in the ratio of 1:1.

The compositions are useful in the treatment of diabetes where in mild cases they may be used as sole treatment or where in more severe cases, where hypoglycaemic agents and/or insulin administration is required, their use can lead to lower or less frequent dosing of these agents.

The compositions are also useful in the treatment of satiety where they afford a feeling in patients of fullness leading to a reduction in food intake.

The invention also includes the use of xanthan gum and locust bean gum in a weight:weight ratio of between 1:9 and 9:1 in the treatment of diabetes and of satiefy.

In a further aspect the invention provides a method of treating diabetes which comprises administering to a subject an orally effective amount of a pharmaceutical composition comprising xanthan gum and locust bean gum in a weight:weight ratio of between 1:9 and 9:1 and preferably in a ratio of between 1:3 and 3:1.

In a further aspect the invention provides a method of treating satiety which comprises administering to a subject an orally effective amount of a pharmaceutical composition comprising xanthan gum and locust bean gum in a weight:weight ratio of between 1:9 and 9:1 and preferably in a ratio of between 1:3 and 3:1.

Xanthan gum and locust bean gum have been used separately as thickeners and emulsifiers in the cosmetic, food and pharmaceutical industries. Locust bean gum is available in a hot-water soluble form and in a cold-water soluble form, a commercial form of the latter being Meyprodyn 200 (Registered Trade Mark, Meyhall Chemical A. G., Kreuzlinga, Switzerland).

The effective oral dose in the treatment of diabetes depends upon the severity of the diabetes and as to whether the compositions comprise the sole therapy or are a part of a multi-drug regime. Generally the dosage form employed will contain 2 to 6 g of the mixed gums with dosing 3 times a day taken before or during meals.

In the treatment of satiety a similar dosage regime is employed.

The compositions will normally be in the form of dry powders or granules which are to be added to water or added to a drink such as tomato juice or orange juice. With hot water dispersible locust bean gums it is necessary to add the compositions to hot liquid (50°–75° C.), but the mixture can then be cooled before administration. Where the compositions do not contain a hot water dispersible locust bean gum they may alternatively be sprinkled onto food.

For the ease of dosing the compositions in the form of powders or granules are conveniently packaged into sachets. A convenient unit dose of the composition in a sachet in the form of powder or granules will comprise from 2 to 6 g of the mixed gums.

The compositions in the form of a fine granular free flowing powder or coarser more discrete granules may include 2.5 to 10%, preferably 5% by weight of the composition of an alcohol soluble binding agent such as polyvinylpyrrolidone. Other binding agents that may be used include ethyl cellulose, methyl cellulose, hydroxypropylmethyl cellulose and hydroxyethyl cellulose.

When the compositions are added to water gelation of the gums takes place. It is desirable therefore that the resultant mixtures are consumed by a patient soon after adding to water otherwise if they are allowed to stand for too long they become too viscous to drink. We have found that the rate of gelation is dependent upon the pH with a lower pH giving slower gelation. Desirably therefore the composition may include 2.5 to 10% by weight of the composition of an organic acid such as citric acid or tartaric acid.

The compositions may also include one or more of a sweetening agent (e.g. saccharin or aspartame), a flavouring agent and/or or a colouring agent.

The invention is illustrated by the following Examples.

EXAMPLE 1

A preparation in the form of granules was prepared from the following formulation:

| | |
|---|---|
| xanthan gum | 1500 g |
| cold water dispersible locust bean gum (Meyprodyn 200) | 1500 g |
| sodium saccharin | 25 g |
| colour, flavouring | 205 g |
| polyvinylpyrrolidone (Kollidon K30 BASF) | 175 g |

The dry powders were screened through a 500 μm sieve before being thoroughly blended. They were then wet granulated using isopropanol and the mass then dried at 50°–60° C. after drying the mass was passed through an appropriate sized sieve to give the required granule size (preferaly 250–750 μm). The granules were packaged into unit dose sachets each containing approximately 2.0, 3.0, 4.0, 5.0, or 6.0 g of the mixed gums.

EXAMPLE 2

The formulation of Example 1 was varied by adding citric acid (250 g) to the mixed powders.

EXAMPLES 3 TO 6

The formulations of Examples 1 and 2 were varied by employing differing amounts of xanthan gum, Meyprodyn 200 and citric acid whilst using the same quantities of sodium saccharin, colour, flavouring and polyvinylpyrrolidone.

|  | 3 | 4 | 5 | 6 |  |
|---|---|---|---|---|---|
| xanthan gum | 750 | 750 | 2250 | 2250 g |
| Meyprodyn 200 | 2250 | 2250 | 750 | 750 g |
| citric acid | — | 250 | — | 250 g |

EXAMPLE 7

The formulations of Examples 1 to 6 can be varied by replacing the cold water dispersible locust bean gum by an equal weight of a hot water dispersible locust bean gum (T. M. Duche & Sons (UK) Ltd).

EXAMPLE 8

The formulations of Examples 1 to 7 can be varied by omitting the binding agent polyvinylpyrrolidone and effecting the wet granulation by using 50% v/v aqueous isopropanol. The gums act as their own binding agents and the use of an isopropanol/water mix enables an even distribution of granulating fluid to be imparted onto the mixed powders.

Diabetic patients often experience problems maintaining a healthy weight there being a tendency for overweight. In the trials with healthy volunteers, discussed below, the compositions when taken before a meal provided a feeling of fullness. The compositions therefore find utility for these persons, whether or not they are diabetics, who have an overweight problem.

The in vitro and in vivo properties of the compositions of the invention have been studied according to the following procedures:

1. In Vitro Studies

In the preliminary studies to determine the relative effects of different polymers on passive glucose diffusion a conventional two compartment dialysis cell as described by Brewster and Muir, Clinical Pharmacology and Therapeutics 27, No. 1, 76-82 (1980) was employed (FIG. 1); solutions of polymer in citric acid:-phosphate buffer at pH=5.4 containing 10% w/v $^{14}C$ glucose were prepared and dialysed across a presoaked cellulose acetate membrane (Spectraphor 2, Registered Trade Mark, MSE Ltd., Crawley, England) into buffer only solution. The dialysis cell was rotated on power driven rollers at 37° C. Dialysis was stopped after one hour, aliquots from the two cells taken, counted by liquid scintillation in the presence of emulsifier scintillation fluid ES299 (Camlab, Cambridge, England) and the amount of $^{14}C$ glucose to diffuse calculated.

Figure 2:
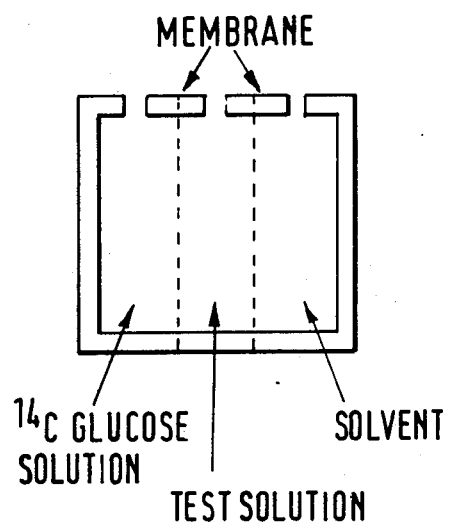

In further studies, a novel three compartment dialysis cell was used in which the test polymer solution in the middle compartment was separated by cellulose acetate membranes from a $^{14}C$ glucose solution on one side and solvent only on the other (FIG. 2). Experiments were carried out using either Ringer Krebs pH=7.4 buffer or water only as the solvent for the polymer and dialysis was terminated after 1.25 hours. The amount of $^{14}C$ glucose to diffuse through the test polymer solution into the solvent only reference cell was calculated.

The effect of various polymers and polymeric mixtures on in vitro diffusion using the two compartment dialysis cell is illustrated in Table 1. In the Table Xn=xanthan gum, LBG=hot water dispersible locust bean gum and percentages are weight/volume (w/v).

TABLE 1

| Polymer | % $^{14}C$ Released* after one hour |
|---|---|
| Control | 96 |
| 1% Guar | 45 |
| 1% Sodium alginate | 99 |
| 1% Ispaghula, NaOH soluble fraction | 100 |
| 0.5% Hydroxyethylcellulose 250 H | 88 |
| 0.5% Xn (unheated) | 68 |
| 1% LBG (unheated) | 89 |
| 0.05% Xn:0.5% LBG: | |
| (i) Unheated | 97 |
| (ii) Heated | 49 |

*Amount of $^{14}C$ in the reference cell, expressed as a % of maximum possible at equilibrium.

The relatively non-viscous polymers such as sodium alginate, hydroxyethylcellulose, Ispaghula and locust bean gum, (which is cold water insoluble) have negligible glucose retaining properties compared to the more viscous guar. Xanthan gum, although less viscous than guar, has an ability in its own right to retain glucose, but this can be further enhanced by addition of locust bean gum. The aqueous Xn:LBG mixture when unheated is relatively non-viscous, but when heated to approximately 75° C., to render the LBG soluble, an interaction between the two gums occur and when subsequently cooled to ambient temperature, a gel is formed.

The results in the three compartment cell are shown in table II where Mn=cold water soluble Meyprodyn 200.

TABLE II

| Polymer (0.1% w/v) | % $^{14}C$ Released into reference cell |
|---|---|
| Xn | 29 |
| LBG | 31 |
| Mn | 25 |
| Xn:LBG (1:1) (heated) | 3 |
| Xn:Mn (1:1) (unheated) | 1 |

Figure 3:
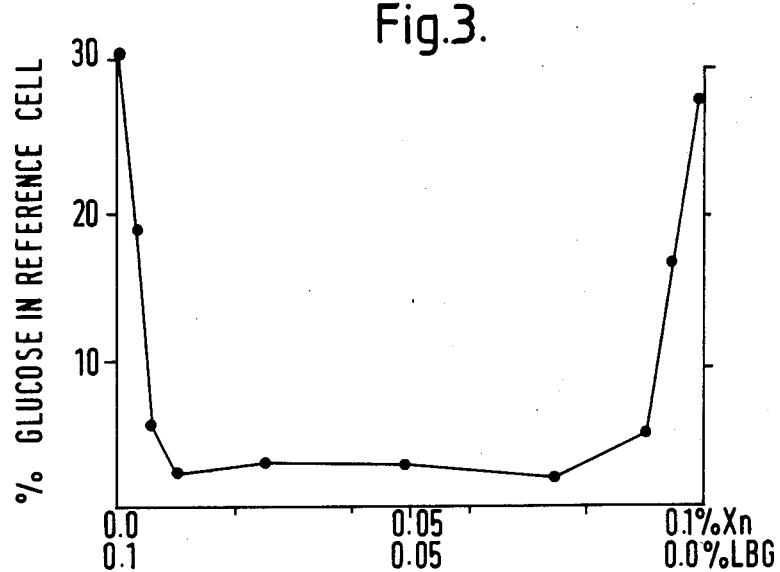
Figure 4:
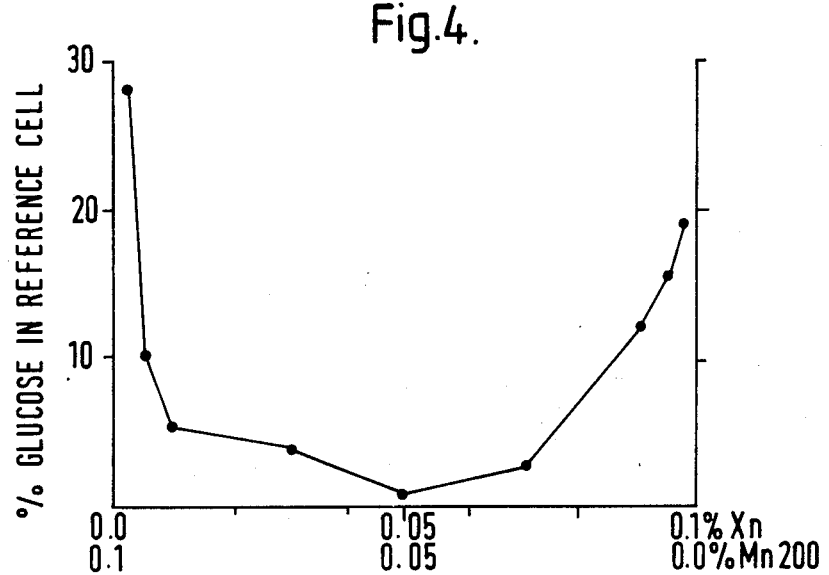

The effect of varying the relative proportions of Xanthan gum and locust bean gum (hot water soluble or the cold water soluble Meyprodyn 200) on glucose diffusion in the three compartment cell is shown in FIGS. 3 and 4. At concentrations of 0.1% the individual gums have negligible effect over control on glucose diffusion in the three compartment dialysis model, but 0.1% Xn:LBG over the range (1:9) to (9:1) and 0.1% Meyprodyn 200 from (1:9) to (7:3) exert a clear synergistic effect over the individual gums.

2. In vivo studies in the rat

The effect of gums in vivo using a tied intestinal loop rat model [based on the method described by Schwenk et al, Naunyn-Schmiedeberg's Arch Pharmacol 321, 223-225 (1982)] has been investigated; male Wister rats (250-280 g) were anaesthetised with barbiturate (ip), the small intestine exposed and a length of jejunum (approximately 20 cms) from the duodenal-jejunal flexure isolated. This segment was cannulated at both ends, flushed with Krebs-bicarbonate Ringer solution and divided into four loops each approximately 5 cm long. Each loop was cannulated at one end and tied at the other. To each loop 1.5 ml of the approximate solution containing $^3H$ glucose and $^{14}C$ carboxylic acid inulin and Krebs bicarbonate Ringer buffer was added and left for twenty minutes, after which time the loop contents were resampled, $^{14}C$ and $^3H$ concentrations determined by liquid scintillation and glucose uptake calculated.

In order to minimise loop effects on glucose uptake the regimen was repeated six times and a total of 24 rats were used. The control solution was Krebs bicarbonate Ringer containing $^3$H glucose and $^{14}$C carboxylic acid inulin. $^{14}$C Carboxylic acid inulin was added to make allowance for any fluid volume change. Statistical analysis of the results was carried out using unpaired t test.

Figure 5:
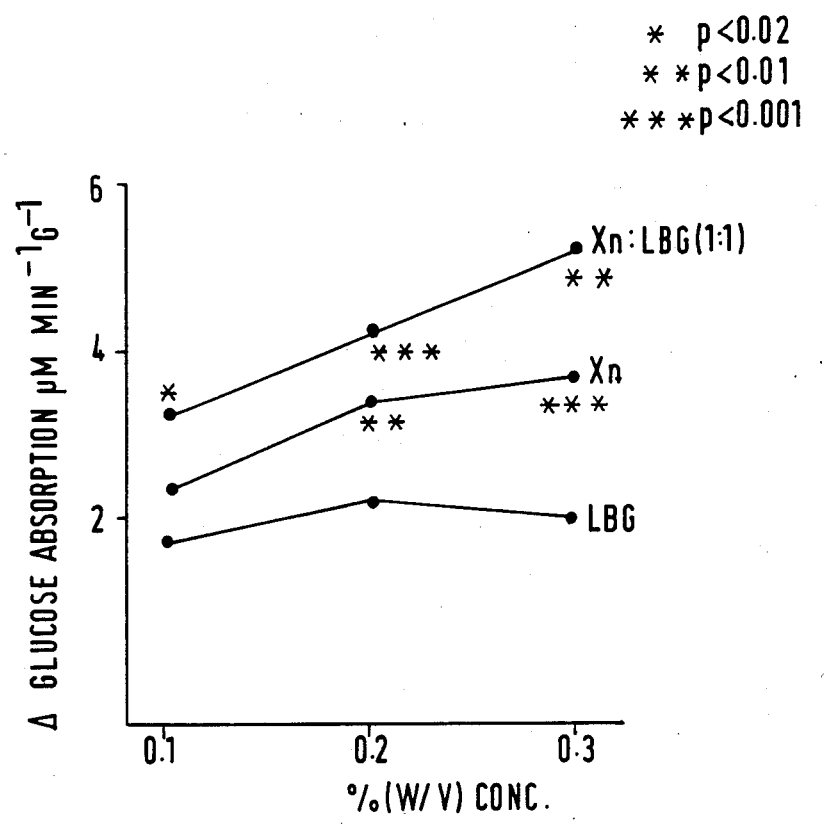

The effect of the gums on glucose absorption in vivo from the rat small intestine tied loop is shown in FIG. 5; the rate of absorption is inhibited by xanthan gum along at concentrations $\geq 0.2\%$ and by Xn:LBG (1:1) at a concentration $\geq 0.1\%$. LBG has been tested at concentrations of up to 0.3% and been found to have no statistically significant effect over control.

2. In vivo studies in man

The effect of gums in man using the oral glucose tolerance test [Watkins, BMJ, 284, 1690, (1982)] has been investigated; in crossover studies up to nine healthy volunteers were given meals consisting of 200 ml distilled water, 500 ml diabetic orange squash and 50 grams glucose with or without 2.5 grams of test material.

The Xn:LBG (1:1) test meal was heated to 75° C. and subsequently cooled before administration to allow the gel to form. For consistency, all other test meals except Xn:Meyprodyn 200 were treated in the same way. Blood samples were drawn from a cannulated forearm vein immediately prior to and at ten minute intervals throughout the study and assayed for blood glucose (Yellow Springs Institute Corporation Glucose Analyser Model 23AM) and insulin (RIA test kit, Washington, NE37 1PP) content.

The Xn, LBG and Xn:LBG studies were carried out in the same group of volunteers. A different group was used in the Xn:Meyprodyn 200 study.

Statistical analysis of results was carried out using the paired t test. Areas under the curve were compared using Simpsons or the Trapezoidal rule.

Figure 6:
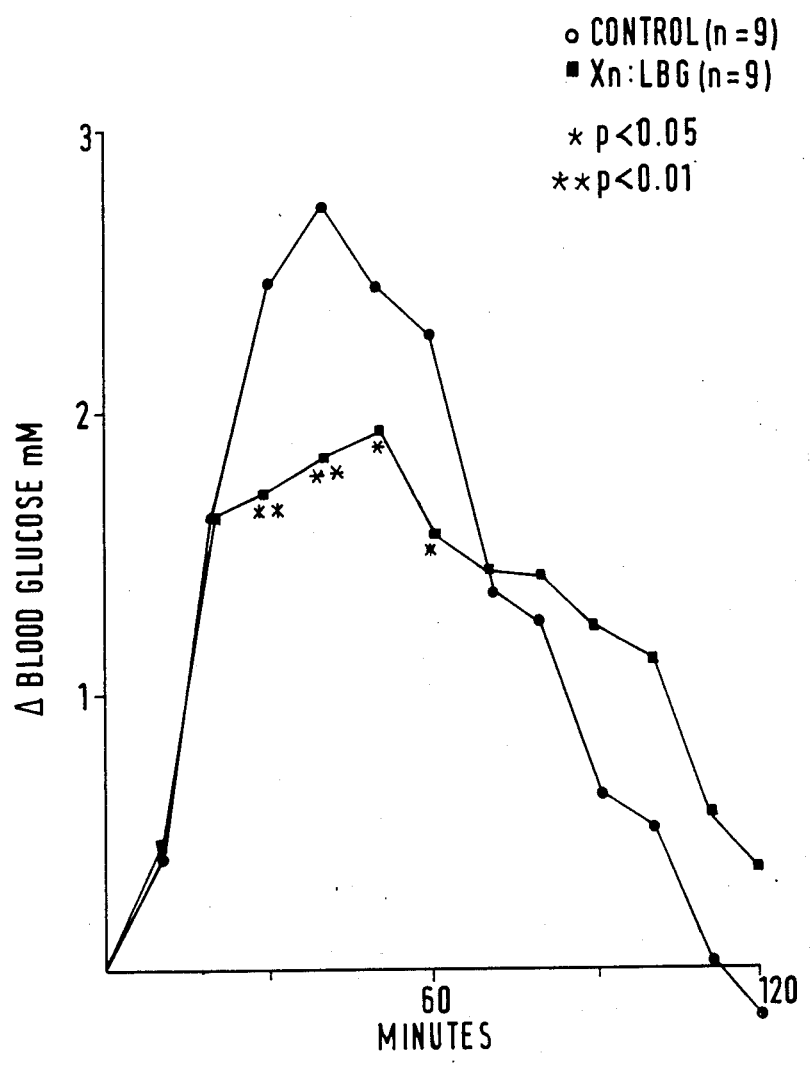
Figure 7:
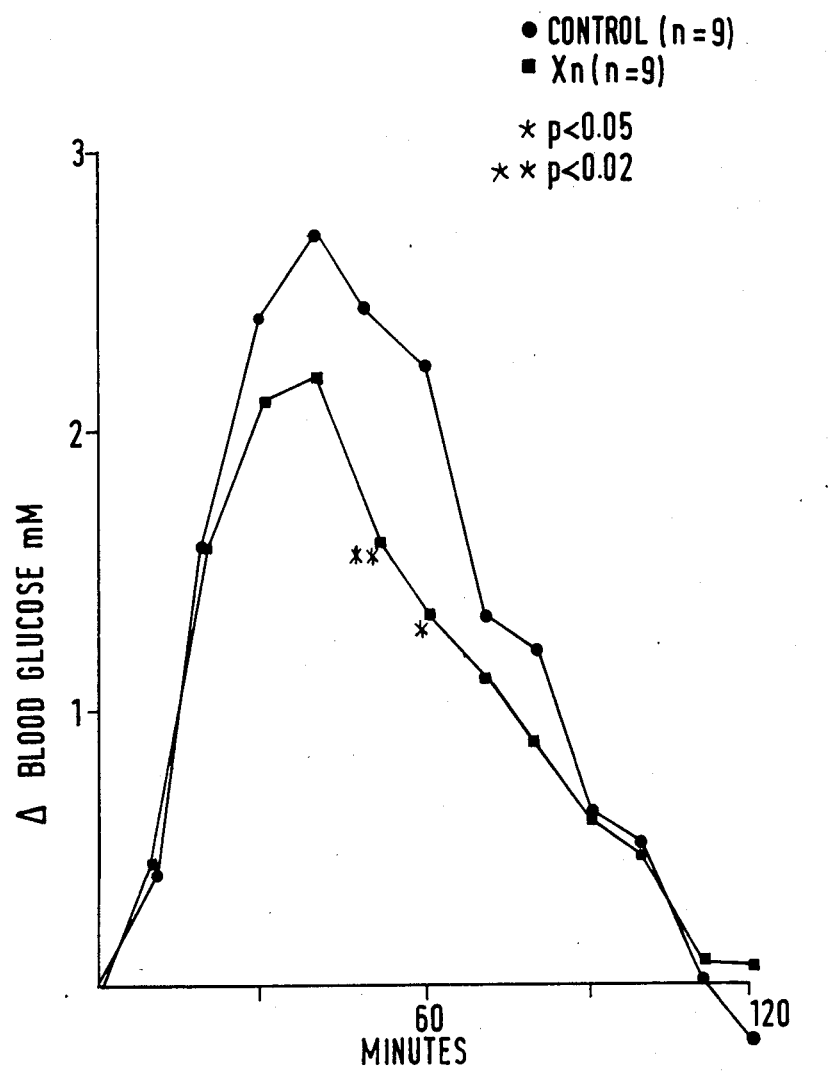
Figure 8:
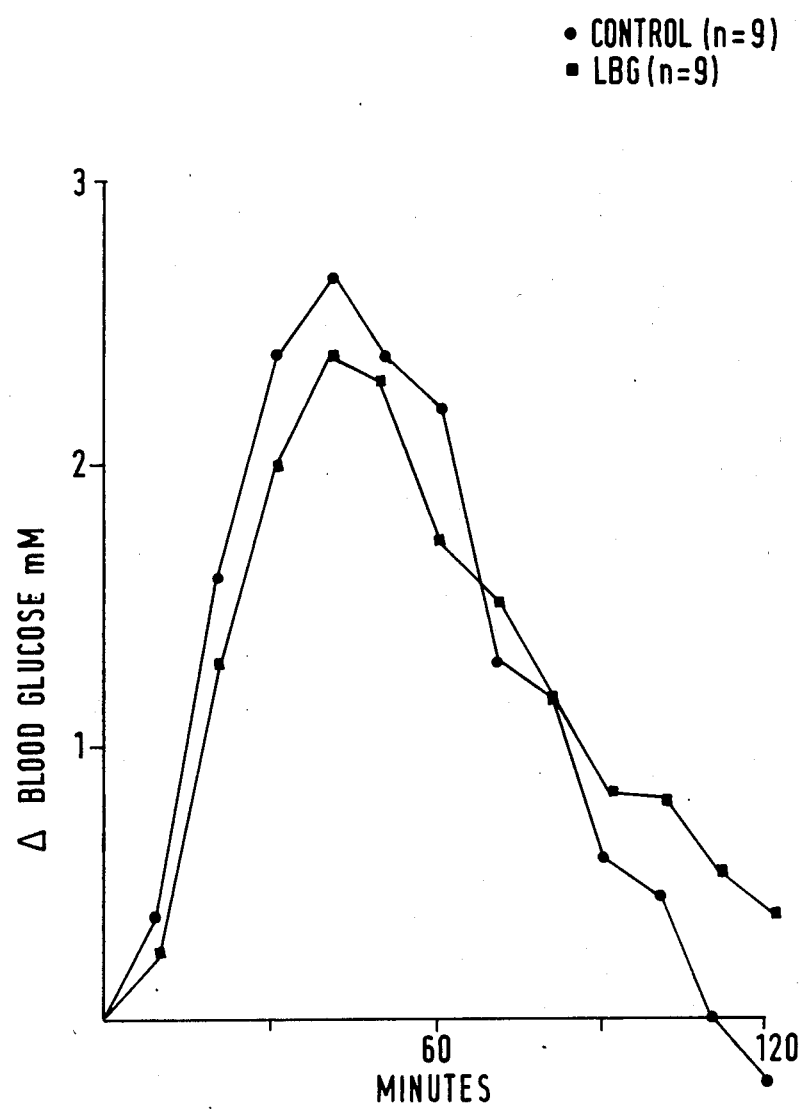
Figure 9:
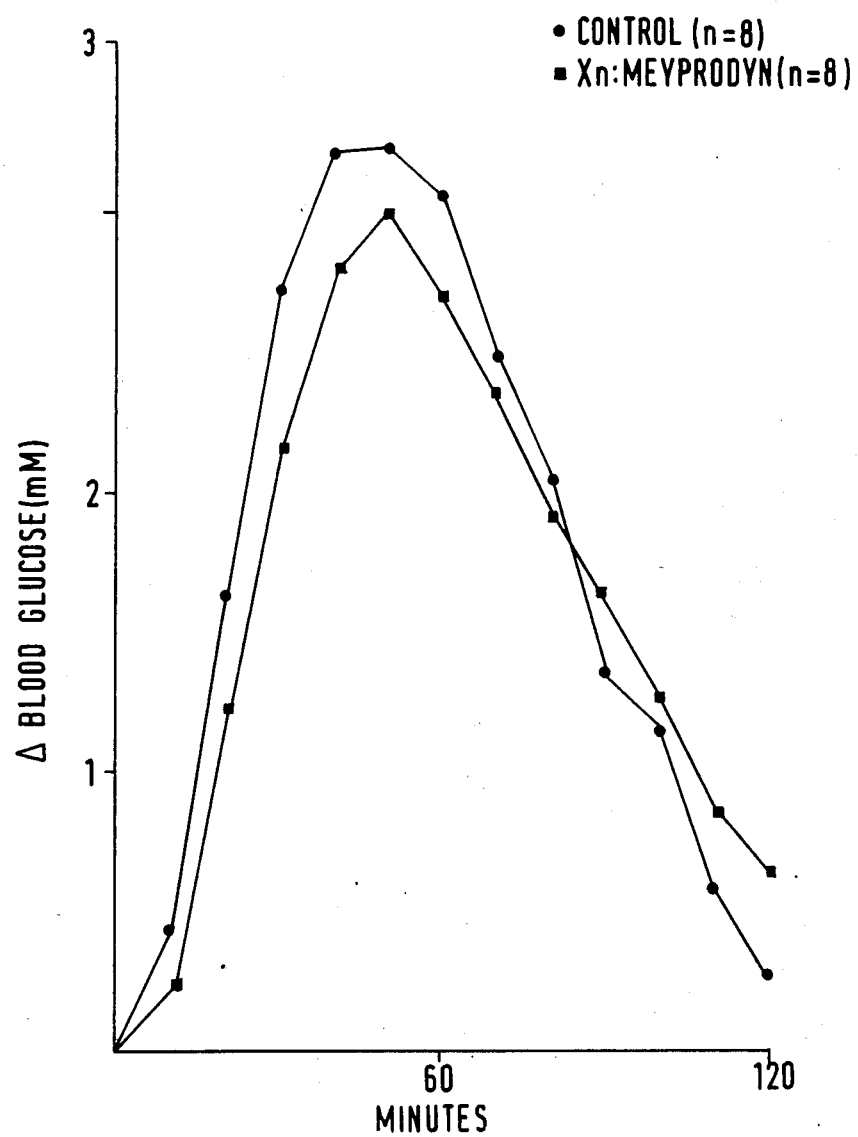

The effect of 2.5 grams Xn:LBG (1:1) on the change in blood glucose levels over basal in healthy volunteers after the 50 gram glucose challenge is illustrated in FIG. 6: the mixture is seen to have a significant effect over control at 30, 40, 50 and 60 minutes indicating that it may be useful in the treatment of hyperglycaemia, particularly if administered at a slightly higher dose. 2.5 Grams Xn was significantly different from control at 50 and 60 minutes (FIG. 7) whereas a similar dose of LBG has no effect at any time point (FIG. 8). No test treatment had any effect on areas under curve after two hours indicating no malabsorption of glucose to have occurred. A limited study (n=3) with 1.25 grams Xn:LBG (1:1) showed no effect at any time point. Neither was any observed with unheated Xn:Meyprodyn 200 (1:1), (n=8), (FIG. 9).

Figure 10:
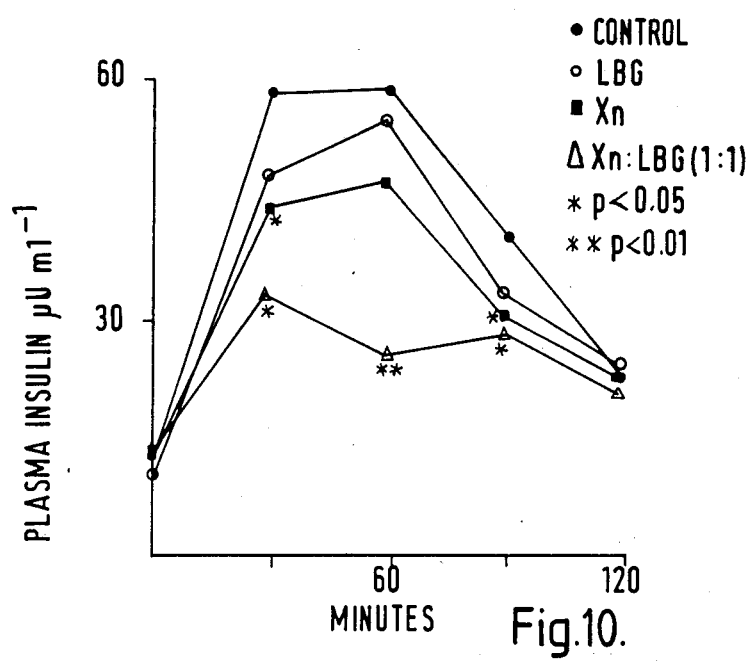
Figure 11:
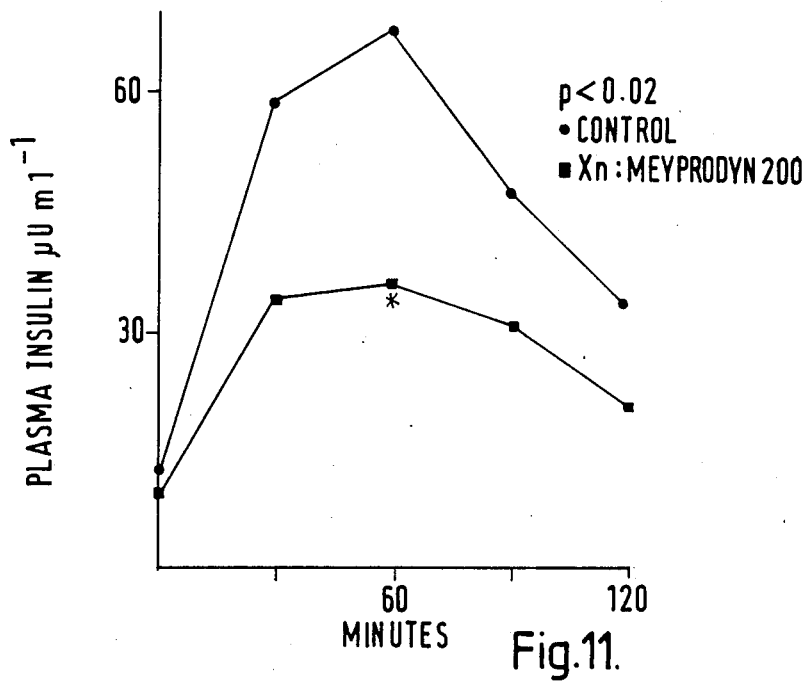

Plasma insulin data was found to be a more sensitive indicator of the action of the polysaccharides than was the glucose data (FIG. 10 and FIG. 11). Insulin levels after 2.5 grams Xn:LBG (1:1) are significantly different from control at 30, 60 and 90 minutes respectively, and after 2.5 grams Xn only treatment at 30 and 90 minutes. 2.5 Grams LBG and 1.25 grams Xn:LBG (1:1) had no significant effect at any time point. After treatment with 2.5 grams Xn:Mn 200 the plasma insulin level at 60 minutes and the area under the curve up to two hours after dosing ($p < 0.05$) are significantly different from control.

We claim:

1. An oral pharmaceutical composition in dry powder or granular form adapted to be added to water or a drink for treatment of diabetes which comprises xanthan gum and locust bean gum in a weight:weight ratio of between 1:9 and 9:1, 2.5 to 10% by weight of the composition of an alcohol soluble binding agent and 2.5 to 10% by weight of the composition of an organic acid.

2. A pharmaceutical composition according to claim 1 which comprises xanthan gum and locust bean gum in a weight:weight ratio of between 1:3 and 3:1, 2.5 to 10% by weight of the composition of an alcohol soluble binding agent and 2.5 to 10% by weight of the composition of an organic acid.

3. A pharmaceutical composition according to claim 1 wherein the locust bean gum is a cold water dispersible locust bean gum.

4. A pharmaceutical composition according to claim 1 wherein the alcohol soluble binding agent is present at 5% by weight.

5. A pharmaceutical composition according to claim 1 wherein the alcohol soluble binding agent is polyvinylpyrrolidone.

6. A pharmaceutical composition according to claim 1 wherein the organic acid is citric acid or tartaric acid.

7. A pharmaceutical composition according to claim 1 in unit dose form and wherein the weight of the mixed gums is between 2 and 6 g.

8. A method of treating diabetes which comprises administering to a subject suffering from diabetes an orally effective amount of a pharmaceutical composition comprising xanthan gum and locust bean gum in a weight:weight ratio of between 1:9 and 9:1 and 2.5 to 10% by weight of the composition of an alcohol soluble binding agent.

9. A method of treating diabetes which comprises administering to a subject suffering from diabetes an orally effective amount of a pharmaceutical composition comprising xanthan gum and locust bean gum in a weight:weight ratio of between 1:3 and 3:1 and 2.5 to 10% by weight of the composition of an alcohol soluble binding agent.

* * * * *

UNITED STATES PATENT AND TRADEMARK OFFICE
CERTIFICATE OF CORRECTION

PATENT NO. : 4,689,219

DATED : August 25, 1987

INVENTOR(S) : Keith SUGDEN

It is certified that error appears in the above-identified patent and that said Letters Patent is hereby corrected as shown below:

Column 1:

Line 14, "9774," should read --7994,--.

Column 4:

Line 63, "approximate" should read --appropriate--.

Column 5:

Line 10, "along" should read --alone--;

Line 15, "2." should read --3.--; and

Line 20, "500 ml" should read --50 ml--.

Signed and Sealed this

Sixth Day of December, 1988

Attest:

DONALD J. QUIGG

*Attesting Officer*  *Commissioner of Patents and Trademarks*